United States Patent
Batzer et al.

(10) Patent No.: US 11,918,366 B2
(45) Date of Patent: Mar. 5, 2024

(54) ELECTROCARDIOGRAM DEVICE FOR USE IN COMBINATION WITH A MAGNETIC RESONANCE DEVICE

(71) Applicant: Siemens Healthcare GmbH, Erlangen (DE)

(72) Inventors: Ulrich Batzer, Spardorf (DE); Michael Roas-Löffler, Erlangen (DE); Christopher Horn, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 18/098,248

(22) Filed: Jan. 18, 2023

(65) Prior Publication Data
US 2023/0225661 A1    Jul. 20, 2023

(30) Foreign Application Priority Data
Jan. 18, 2022   (DE) .......................... 102022200550.3

(51) Int. Cl.
*A61B 5/05* (2021.01)
*A61B 5/055* (2006.01)
*A61B 5/33* (2021.01)

(52) U.S. Cl.
CPC ................ *A61B 5/33* (2021.01); *A61B 5/055* (2013.01)

(58) Field of Classification Search
CPC .................................. A61B 5/33; A61B 5/055
See application file for complete search history.

(56) References Cited

U.S. PATENT DOCUMENTS

| 6,148,229 | A | 11/2000 | Morris, Sr. et al. |
| 2005/0288572 | A1* | 12/2005 | Graw ............... A61B 6/541 |
| | | | 600/407 |
| 2011/0082359 | A1 | 4/2011 | Rey |
| 2015/0094561 | A1 | 4/2015 | Rey et al. |
| 2016/0279405 | A1* | 9/2016 | Riley ............... G16H 50/20 |
| 2016/0310037 | A1 | 10/2016 | O'Neill et al. |
| 2017/0000374 | A1 | 1/2017 | O'Neill et al. |
| 2017/0135580 | A1* | 5/2017 | Lips ............... A61B 5/055 |
| 2021/0290136 | A1* | 9/2021 | Von Bergen ........ A61B 5/282 |

FOREIGN PATENT DOCUMENTS

| CN | 102065758 A | 5/2011 |
| CN | 105916442 A | 8/2016 |
| DE | 202021104314 U1 | 9/2021 |

OTHER PUBLICATIONS

Abi-Abdallah, D., Robin, V. et al: "Alterations in Human Ecg Due To The Magnetohydrodynamic Effect: A Method for Accurate R Peak Detection In The Presence Of High MHD Artifacts", in Conference proceedings: Annual International Conference of the IEEE Engineering in Medicine and Biology Society. IEEE Engineering in Medicine and Biology Society. Conference Feb. 2007, DOI:10.1109/IEMBS.2007.4352673.

\* cited by examiner

*Primary Examiner* — Joel F Brutus
(74) *Attorney, Agent, or Firm* — Banner & Witcoff Ltd.

(57) ABSTRACT

An electrocardiography device (ECG device) designed for use in combination with a magnetic resonance device, including: a carrier unit; a receiving unit designed to mount on the carrier unit; an electrode; an electrode conductor connecting the electrode to the receiving unit, wherein the electrode conductor is stabilized at least partially by way of a shapeable guide element.

11 Claims, 5 Drawing Sheets

ELECTROCARDIOGRAM DEVICE FOR USE IN COMBINATION WITH A MAGNETIC RESONANCE DEVICE

TECHNICAL FIELD

The disclosure relates to an electrocardiography device (ECG device) for using in combination with a magnetic resonance device, a magnetic resonance device comprising such an ECG device and a method for capturing an ECG signal.

BACKGROUND

In a magnetic resonance device, the body to be examined of an examination object, particularly that of a patient, is typically exposed to a relatively strong main magnetic field of, for example, 1.5 or 3 or 7 tesla, with the aid of a main magnet. In addition, with the aid of gradient pulses and radio frequency pulses, radio frequency signals are induced in nuclear spins, which are received by means of suitable radio frequency antennas and are reconstructed to form image data. The temporal sequence of the gradient pulses and radio frequency pulses is typically specified by MR control sequences. These MR control sequences can be synchronized with the heartbeat of the patient, which is advantageous particularly in cardiological examinations. For this purpose, an electrocardiogram of the patient can be recorded before or during a magnetic resonance examination. This typically takes place at a time point at which the patient is positioned within the magnetic resonance device and is exposed to the main magnetic field. Herein, this involves interactions between the main magnetic field, physical effects resulting therefrom and the ECG device.

In particular, the magnetohydrodynamic (MHD) effect, arising due to the blood flow of an examination object situated in the magnetic field, is a known interaction of this type, as published, for example in "Alterations in human ECG due to the MagnetoHydroDynamic effect: A method for accurate R peak detection in the presence of high MHD artifacts", Abi-Abdallah et al., 2007, 29th Annual International Conference of the IEEE Engineering in Medicine and Biology Society. The MHD effect typically causes an enlargement of the T-wave in an electrocardiogram. This effect can be reduced by a positioning of electrodes of the ECG device on the upper body of the patient, which is not precisely defined among specialists, but relies upon values based upon the experience of the medical personnel.

SUMMARY

It is an object of the disclosure to provide an easily used device for generating a reliable electrocardiogram. The object is achieved with the features of the independent claims. Advantageous aspects are disclosed in the subclaims.

The electrocardiography device (ECG device) according to the disclosure designed for use in combination with a magnetic resonance device comprises: a carrier unit; a receiving unit designed for mounting on the carrier unit; an electrode; and an electrode conductor connecting the electrode to the receiving unit, wherein the electrode conductor is stabilized at least partially by way of a shapeable guide element.

An electrode is typically designed to be arranged on a skin and/or surface of an examination object, in particular, removably fixed. An electrode preferably comprises a sensor that is designed to capture an electrical signal emerging from the body, in particular emerging from a heart movement and/or heart stimulation of the examination object. An electrode typically comprises an electrode connection to which an electrode conductor, preferably exactly one electrode conductor, connects. The connection between the electrode conductor and the electrode can be designed as releasable and/or permanent.

The electrode can be designed as an adhesive electrode. The ECG device preferably comprises at least three electrodes.

Each electrode conductor is typically designed to connect one electrode to the receiving unit. The electrode conductor typically comprises an electrically conductive cable which is preferably insulated outwardly. The electrode conductor is typically designed to transfer an ECG signal captured by the electrode connected to the electrode conductor to the receiving unit. The ECG device preferably comprises at least three electrode conductors, wherein exactly one electrode conductor of the at least three electrode conductors can connect one electrode to the receiving unit.

The receiving unit is preferably configured to bring together and/or process and/or evaluate ECG signals captured by means of the at least one electrode, preferably captured by two or three or four electrodes. The receiving unit can comprise a filter unit configured to filter an ECG signal and/or an amplifier unit configured to amplify an ECG signal. The receiving unit can also comprise a status unit which is configured to identify the functionality and/or use of at least one electrode. The receiving unit can comprise a processor unit which is designed to evaluate the at least ECG signals from a plurality of electrodes and/or to generate an ECG on the basis thereof.

The receiving unit is preferably connected to an ECG control unit. The ECG control unit can be arranged within an RF-screened room in which the magnetic resonance device is also arranged.

The ECG control unit can be arranged outside an RF-screened room in which the magnetic resonance device is also arranged. The ECG control unit is typically connected to the magnetic resonance device, in particular to a control unit included by the magnetic resonance device. The receiving unit is preferably arranged on the carrier unit.

The carrier unit is preferably designed to fix and/or stabilize and/or arrange the receiving unit in a position decoupled from an examination object, in particular decoupled from a movement of the examination object and/or at a defined spacing from a magnetic resonance device and/or at a defined spacing from a patient table if the receiving unit is arranged and/or mounted on the carrier unit. The carrier unit is preferably designed to accommodate the receiving unit. The receiving unit is preferably able to be mounted detachably on the carrier unit. The carrier unit is preferably designed so that the receiving unit can be positioned above the examination object. The carrier unit preferably has a position at which the receiving unit is to be arranged. The position typically has a spacing of between 2 cm and 30 cm, preferably between 5 cm and 20 cm, particularly preferably between 7 cm and 15 cm from a ribcage of an average examination object when this examination object is arranged on a patient table and/or at least partially surrounded by the carrier unit and/or in the patient receiving region of a magnetic resonance device in the context of a combined capture of MR signals and ECG signals. The carrier unit is preferably designed so that the position intended for the receiving unit is arranged above the ribcage of the examination object.

According to the disclosure, the electrode conductor is stabilized by at least one shapeable guide element. The shapeable guide element is preferably manually shapeable in an inelastic manner and/or manually shapeable in a plastic manner and/or stiffly shapeable. The shapeable guide element is preferably suitable to be oriented and/or deformed by medical personnel so that the electrode lies on the body surface of the examination object. The shapeable guide element is preferably designed as elongate and/or at least partially surrounds the electrode conductor. The electrode conductor is preferably connected to the shapeable guide element and/or is arranged parallel thereto. The electrode conductor can be integrated into the shapeable guide element and/or abut its surface.

It has been recognized that in addition to the MHD effect in the electrocardiogram, interferences occur in the isoelectric region. It has been recognized that these disturbances are attributable to a movement of at least one electrode conductor. The movement can be induced, for example, by the pulse of the examination object, whereby electrode conductors can be induced to oscillate. Since the electrode conductors are exposed, during use of the ECG device in the magnetic resonance device, to the main magnetic field, on a movement of the electrode conductors an interference occurs in the ECG signals. In particular, oscillations with frequencies in the range of the frequencies of an ECG can be excited and distort said ECG. A filtration of frequencies induced by such oscillations is particularly difficult.

The receiving unit, designed for mounting on the carrier unit, in combination with an electrode conductor stabilized by a shapeable guide element which connects the electrode, preferably arranged on the body surface of the examination object, to the receiving unit, reduces the movement of the ECG device and/or the electrode conductor. In particular, a transmission of a movement of the examination object due, for example, to breathing, heartbeat and/or controlled movement, to the electrode conductor and/or the receiving unit can be prevented. In addition, the shapeable guide element can eliminate and/or reduce a movement of the electrode conductor due to electromagnetic interaction with the magnetic resonance device. The ECG device according to the disclosure enables the electrode conductor to be held still as close as possible to the body surface of the examination object. By this means, it is largely mechanically decoupled from respiratory, pulse and other movements of the patient. In particular, the inelastically shapeability of the shapeable guide element enables a robust connection between the receiving unit and the electrode.

This increases the quality of the ECG signal and enables a diagnostic precision of the ECG signal within the magnetic resonance device, in particular, provided the magnetic field gradients are switched off during the capture of the ECG signal. Heartbeats can thus be captured reliably and used for triggering an MR control sequence. In addition, particularly by reason of the carrier unit, the ECG device can be constructed reliably and robustly and enables the examination object to make an examination free of loose cables and exposed components. The ECG device according to the disclosure is thus configured for a particularly precise generation of an electrocardiogram which is error-minimized, in particular in the isoelectric region.

One aspect of the ECG device provides that the shapeable guide element comprises at least one of the following components for a stabilizing effect: MR-insensitive metal wire; aluminum wire; copper wire; and flexibly mutually engaging and connected hemispheres and/or spheres.

Flexibly mutually engaging and connected hemispheres and/or spheres are typically used, in particular, for tripods for cameras, so-called gorillapods. Stands of this type are stable and economically commercially available, in particular in suitable lengths of up to 25 cm. Stands of this type are preferably made entirely from plastic. In addition, flexibly mutually engaging and connected hemispheres and/or spheres can readily be manually bent so that they can readily be adapted to the individual anatomy of the examination object. The positioning of the electrodes is highly relevant for the conclusiveness of an ECG. The use of an MR-insensitive metal wire such as, for example, aluminum and/or copper is usable particularly economically and robustly. An MR-insensitive metal wire preferably comprises exclusively diamagnetic metal. In addition, such shapeable guide elements can be easily retrofitted for ECG devices in existing commercial usage. The components mentioned can be deformed steplessly and enable particularly good stabilization of the electrode conductor, individually adapted to the anatomy of the examination object.

The components can have a sheathing. This improves hygiene, in particular, and the possibility of cleaning the shapeable guide element well.

One aspect of the ECG device provides that the shapeable guide element has a length of between 5 cm and 25 cm, preferably between 10 cm and 20 cm, particularly preferably between 13 cm and 17 cm. This length enables individual stabilization of the electrode conductor dependent upon the height and chest circumference of the examination object and thus a particularly low-movement positioning of the electrode on the required site on the ribcage of the examination object.

One aspect of the ECG device provides that the length of the shapeable guide element corresponds to at least 80%, preferably at least 90%, of the length of the electrode conductor. The shapeable guide element is intended, firstly, to stabilize the electrode conductor over the largest possible range of its length to minimize and/or eliminate movements and, in particular, oscillations and/or vibrations of the electrode conductor. Secondly, it is required that the electrode conductor is movable at least in parts in order to be able to yield to a movement of the ribcage without the electrode fixed on the ribcage detaching from the ribcage. This aspect enables stability with simultaneous flexibility of the electrode conductor.

One aspect of the ECG device provides that, starting from the end of the electrode conductor adjoining the electrode, a length of between 0.3 cm and 3 cm, preferably between 0.5 cm and 2.5 cm, particularly preferably between 1 cm and 2 cm of the electrode conductor is free of a stabilization by the shapeable guide element. This enables a mobility of the electrode conductor in the direct vicinity of the electrode and thus for fixing on the examination object. This increases the level of comfort for the examination object and reduces the probability that the electrode can detach from the body surface of the examination object. However, from the part of the electrode conductor that is free of a stabilization by the shapeable guide element, only greatly reduced vibrations are to be expected, said vibrations having a greatly reduced amplitude and frequencies that lie outside the frequency range of relevance for an ECG. This aspect enables stability with simultaneous flexibility of the electrode conductor.

One aspect of the ECG device provides that the carrier unit is designed for mounting on a patient table. The carrier unit is preferably able to be detachably fixed on the patient table. This simplifies, in particular, the preparation of the ECG examination in combination with an MRI examination.

The ECG device can be readily attached to the examination object, in particular also in the lying position of the examination object. In addition, it is thereby ensured that the ECG device is firmly fixed on a displacement of the patient table relative to the examination object.

One aspect of the ECG device provides that the carrier unit comprises a fixing unit designed for accommodating the receiving unit. The fixing unit enables the electrodes, the electrode conductor and the receiving unit to be already attached to an examination object outside the room in which the magnetic resonance device is arranged. This is particularly convenient since the electrodes, the electrode conductor and the receiving unit typically weigh less than 800 grams and are thus easy to handle and transport. Only after positioning of the examination object on the patient table can the receiving unit be arranged on the fixing unit of the carrier unit. This shortens the duration for which the examination object occupies the space of the magnetic resonance device and increases the throughput of patients.

One aspect of the ECG device provides that the carrier unit comprises a manually stiffly shapeable carrier structure. The manually stiffly shapeable carrier structure can be designed, for example, as a deformable arm which can be fastened on one side of the patient table and/or with a strap underneath the examination object. The manually stiffly shapeable carrier structure is preferably designed in parts similarly to the shapeable guide element. The manually stiffly shapeable carrier structure preferably comprises at least two stable elongate structures which are arranged by means of at least one stiffly shapeable guide element movable relative to one another, wherein the at least one stiffly shapeable guide element is manually shapeable and apart from an intended deformation, retains its shape stably. The manually stiffly shapeable carrier structure can be designed to be easily flexible in order to dampen slight movements. This aspect enables, in particular, a good handling since the upper body of the examination object and thus also electrodes positioned thereon, and the receiving unit and the electrode conductor are easily accessible and can thus be favorably arranged.

One aspect of the ECG device provides that the carrier unit comprises a stable frame for positioning above a ribcage of an examination object. This stable frame is preferably designed as the surface of a half-cylinder and/or a half-polyhedron, penetrated by areal openings. A carrier unit of this type can be reliably and robustly positioned at a defined separation from the ribcage of the examination object, in particular when fixing on the patient table.

One aspect of the ECG device additionally comprises a movement sensor unit arranged on the electrode conductor and/or the shapeable guide element, designed for capturing a movement of the electrode conductor. This aspect enables a continuous testing of the quality of the ECG signal captured by the ECG device, since the influence, in particular, of the movement of the electrode conductor on the quality of the ECG signal has been recognized.

One aspect of the ECG device provides that the movement sensor unit comprises a movement detection unit and a first electrical conductor and the movement detection unit is designed to capture the movement of the electrode conductor on the basis of a continuous measurement of an electrical resistance in the first electrical conductor.

The first electrical conductor can correspond to the electrode conductor. The first electrical conductor can be different from the electrode conductor. The continuous measurement of the electrical resistance in the first electrical conductor preferably takes place quasi-continuously, in particular by way of measuring the electrical resistance at temporal intervals of no more than 1 ms. The first conductor is preferably particularly resistance-sensitive, in particular with regard to a movement of the electrode conductor and/or the shapeable guide element. The movement detection unit preferably comprises an analogue-to-digital converter and a power source designed for generating an electrical current in the first electrical conductor. This aspect enables a particularly space-saving, easy to realize and sensitive possibility for capturing a movement of the electrode conductor.

Furthermore, the disclosure relates to a method for capturing an ECG signal of an examination object using the ECG device according to the disclosure in combination with a capture of MR signals of the examination object by means of a magnetic resonance device, according to the following method steps: capturing an MR signal of the examination object; and capturing an ECG signal of the examination object.

The capture of the MR Signal preferably takes place simultaneously with the capture of the ECG signal.

One aspect of the method according to the disclosure provides for the use of the ECG device according to the disclosure additionally comprising the movement sensor unit and a capture of a movement of the electrode conductor, wherein after a captured movement of the electrode conductor, at least one of the following method steps is carried out: rejection of the ECG signal; correction of the ECG signal; indication of the captured movement to the magnetic resonance device; rejection of the MR signal; and correction of the MR signal.

Preferably at least one threshold value is provided to the method for a movement and/or for a change in the resistance in the first electrical conductor. Dependent upon the size of the captured movement of the electrode conductor relative to the at least one threshold value, at least one of the method steps mentioned can be carried out. The rejection of the ECG signal typically comprises ignoring and/or deleting the ECG signal which was captured within a time segment of the captured movement, in particular a captured movement greater than a threshold value. The rejection of the MR signal typically comprises ignoring and/or deleting the MR signal which was captured within a time segment of the captured movement, in particular a captured movement greater than a threshold value. The correction of the ECG signal and/or of the MR signal can take place taking account of a specific movement form such as a movement of the ribcage due to breathing. The correction of the ECG signal and/or of the MR signal can also take place taking account of individual data, in particular physiological data of the examination object. The indication of the captured movement to the magnetic resonance device preferably takes place by way of signaling the captured movement from the ECG control unit to the control unit of the magnetic resonance device.

Further aspects of the method according to the disclosure are configured similarly to the aspects of the ECG device according to the disclosure.

Furthermore, the disclosure relates to a magnetic resonance device comprising a detector unit designed to record an MR signal of an examination object which is arranged within a patient receiving region at least partially surrounded by the detector unit. The magnetic resonance device further comprises an ECG device according to the disclosure, said ECG device being arranged within the patient receiving region and being designed to capture an ECG signal from the examination object, in particular when the examination object is arranged within the patient receiving region. The magnetic resonance device further comprises an ECG control unit comprising a movement correction unit. The ECG control unit is configured to carry out a disclosed method for capturing an ECG signal.

For this purpose, the ECG control unit typically has an input, a processor unit and an output. Via the input, functions, algorithms or parameters needed in the method can be provided to the ECG control unit. The ECG signal and/or further results of an aspect of the method according to the disclosure can be provided via the output. The ECG control unit can be integrated into the magnetic resonance device. The ECG control unit can also be installed separately from the magnetic resonance device. The ECG control unit can be connected to the magnetic resonance device.

Aspects of the magnetic resonance device according to the disclosure are configured similarly to the aspects of the method according to the disclosure and the ECG device according to the disclosure. The magnetic resonance device can have further determining components which are necessary and/or advantageous for carrying out a disclosed method. The magnetic resonance device can also be designed to transmit control signals and/or to receive and/or process control signals in order to carry out a disclosed method. Preferably, the ECG control unit is part of the control unit of the magnetic resonance device according to the disclosure. In a memory store unit of the ECG control unit, computer programs and other software can be stored, by means of which the processor unit of the ECG control unit automatically controls and/or carries out a sequence of a disclosed method.

A computer program product according to the disclosure can be loaded directly into a memory store unit of a programmable ECG control unit and has program code means in order to carry out a disclosed method when the computer program product is executed in the ECG control unit. In this way, the method according to the disclosure can be carried out in a rapid, exactly reproducible and robust manner. The computer program product is configured so that it can carry out the method according to the disclosure steps by means of the ECG control unit. The ECG control unit has the respective pre-conditions such as, for example, a suitable working memory store, a suitable graphics card or a suitable logic unit so that the respective method steps can be carried out efficiently. The computer program product is stored, for example, on an electronically readable medium or is deposited on a network or server from where it can be loaded into the processor of a local ECG control unit which can be directly connected to the magnetic resonance device or configured as part of the magnetic resonance device. Furthermore, control information of the computer program product can be stored on an electronically readable data carrier. The items of control information of the electronically readable data storage medium can be configured such that they carry out a disclosed method when the data carrier is used in an ECG control unit of a magnetic resonance device. Examples of electronically readable data carriers are a DVD, a magnetic tape or a USB stick, on which electronically readable control information, in particular software, is stored. If this control information (software) is read from the data carrier and stored in a control unit and/or an ECG control unit of a magnetic resonance device, the aspects according to the disclosure of the above-described method can be carried out.

The disclosure also relates to an electronically readable data carrier on which a program is stored which is provided for carrying out a method for capturing an ECG signal of an examination object.

The advantages of the magnetic resonance device according to the disclosure, the computer program product according to the disclosure, the electronically readable data carrier according to the disclosure and the method according to the disclosure for capturing an ECG signal of an examination object substantially correspond to the advantages of the ECG device according to the disclosure, as described in detail above. Features, advantages or alternative aspects mentioned herein can also be transferred to the other claimed subject matter and vice versa.

BRIEF DESCRIPTION OF THE DRAWINGS

Further advantages, features and details of the disclosure will become apparent from the description below of exemplary aspects and from the drawings, in which.

DETAILED DESCRIPTION

Figure 1:
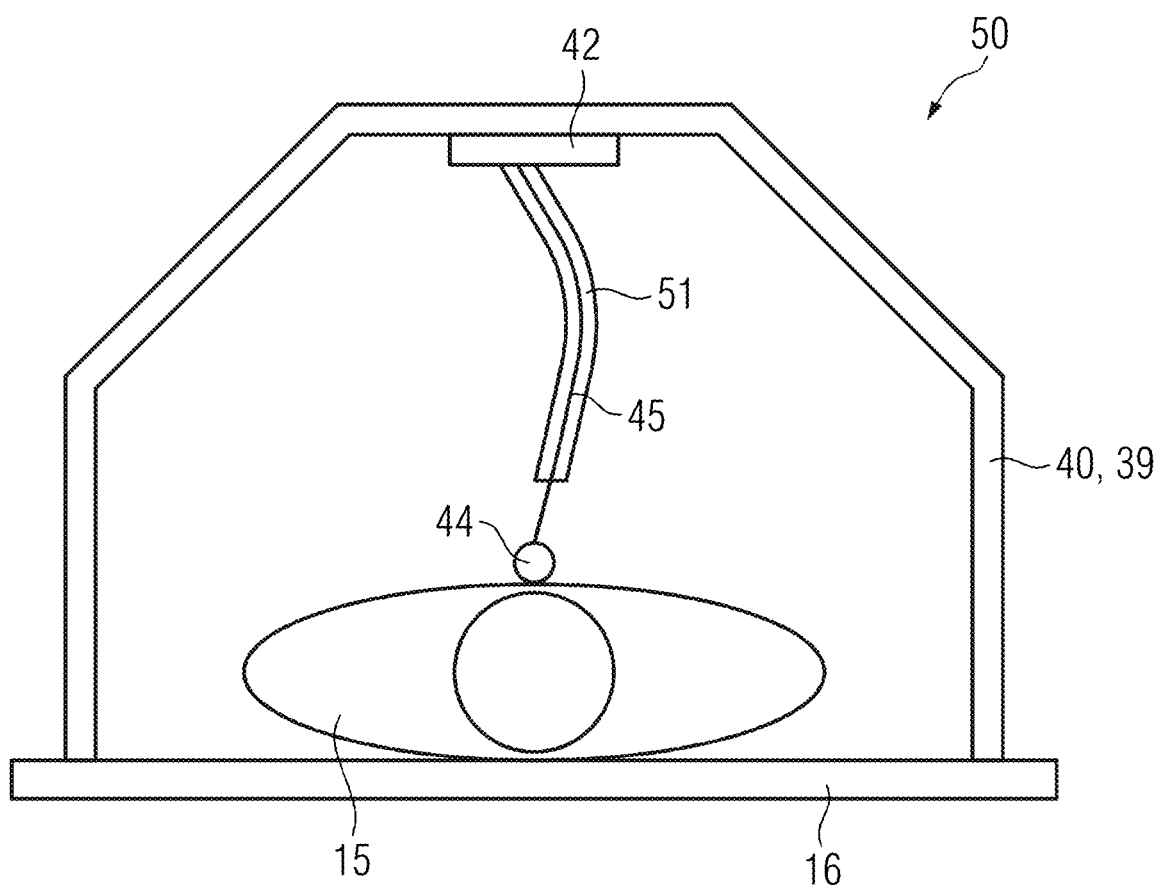
FIG. 1 shows a first aspect of an ECG device according to the disclosure in a schematic representation.

FIG. 1 shows a first aspect of an ECG device 50 according to the disclosure for use in combination with a magnetic resonance device 11 in a schematic representation. The ECG device 50 comprises a carrier unit 40 and a receiving unit 42 designed for mounting on the carrier unit 40. In addition, the ECG device 50 comprises an electrode 44 and an electrode conductor 45 connecting the electrode 44 to the receiving unit 42, wherein the electrode conductor 45 is stabilized at least partially by a shapeable guide element 51. The ECG device 50 comprises the shapeable guide element 51. The shapeable guide element 51 has a length of between 5 cm and 25 cm. The length of the shapeable guide element 51 corresponds to at least 80% of the length of the electrode conductor 45. Starting from the end of the electrode conductor 45 adjoining the electrode 44, between 0.5 cm and 3 cm of the electrode conductor 45 is free of a stabilization by the shapeable guide element 51. The carrier unit 40 is designed for mounting on a patient table 16. The carrier unit 40 can comprise a stable frame 39 for positioning above a ribcage of an examination object 15.

Figure 2:
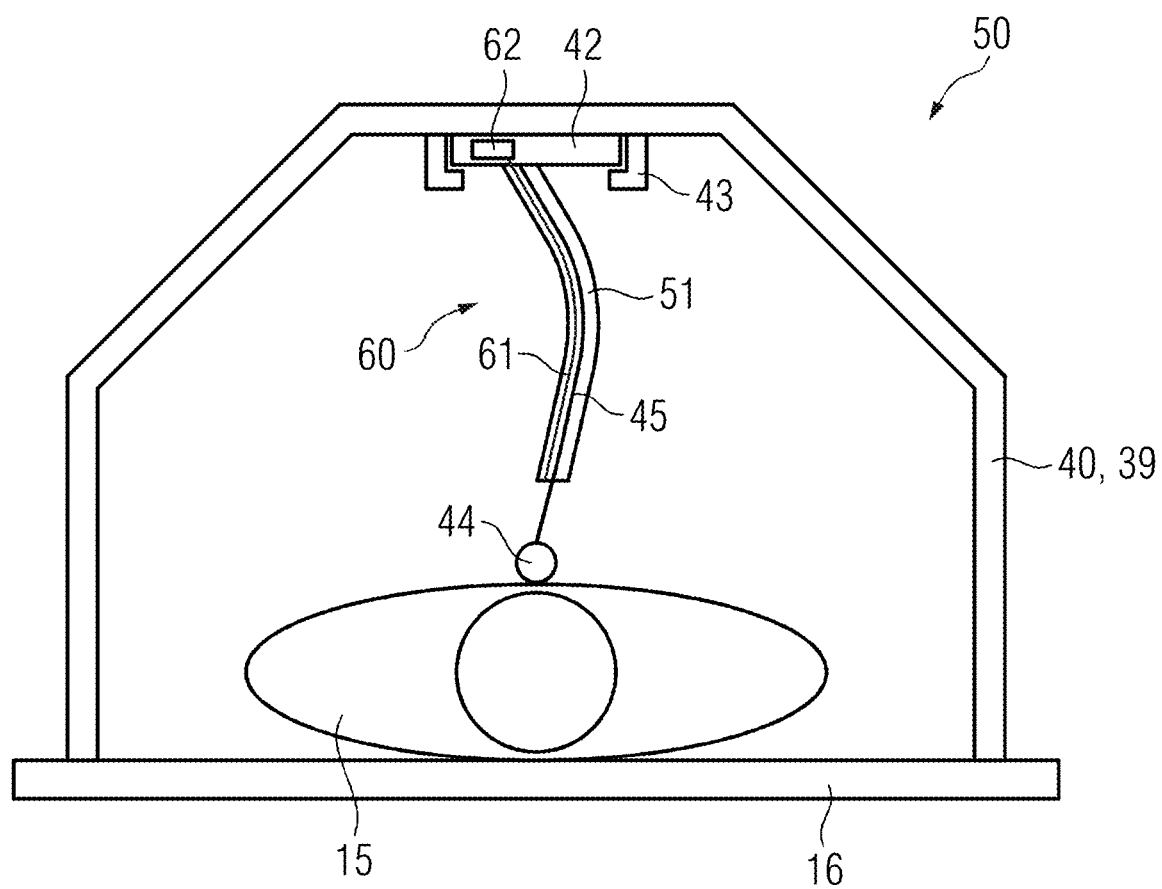
FIG. 2 shows a second aspect of an ECG device according to the disclosure in a schematic representation.

FIG. 2 shows a second aspect of an ECG device 50 according to the disclosure in a schematic representation. The second aspect differs from the first aspect shown in FIG. 1 in that the carrier unit 40 comprises a fixing unit 43 which is designed for accommodating the receiving unit 42. In addition, according to this aspect, the ECG device 50 comprises a movement sensor unit 60 arranged on the electrode conductor 45 and/or the shapeable guide element 51, configured for capturing a movement of the electrode conductor 45. The movement sensor unit 60 comprises a movement detection unit 62 and a first electrical conductor 61. The movement detection unit 62 is designed to capture the movement of the electrode conductor 45 on the basis of a continuous measurement of an electrical resistance in the first electrical conductor 61.

Figure 3:
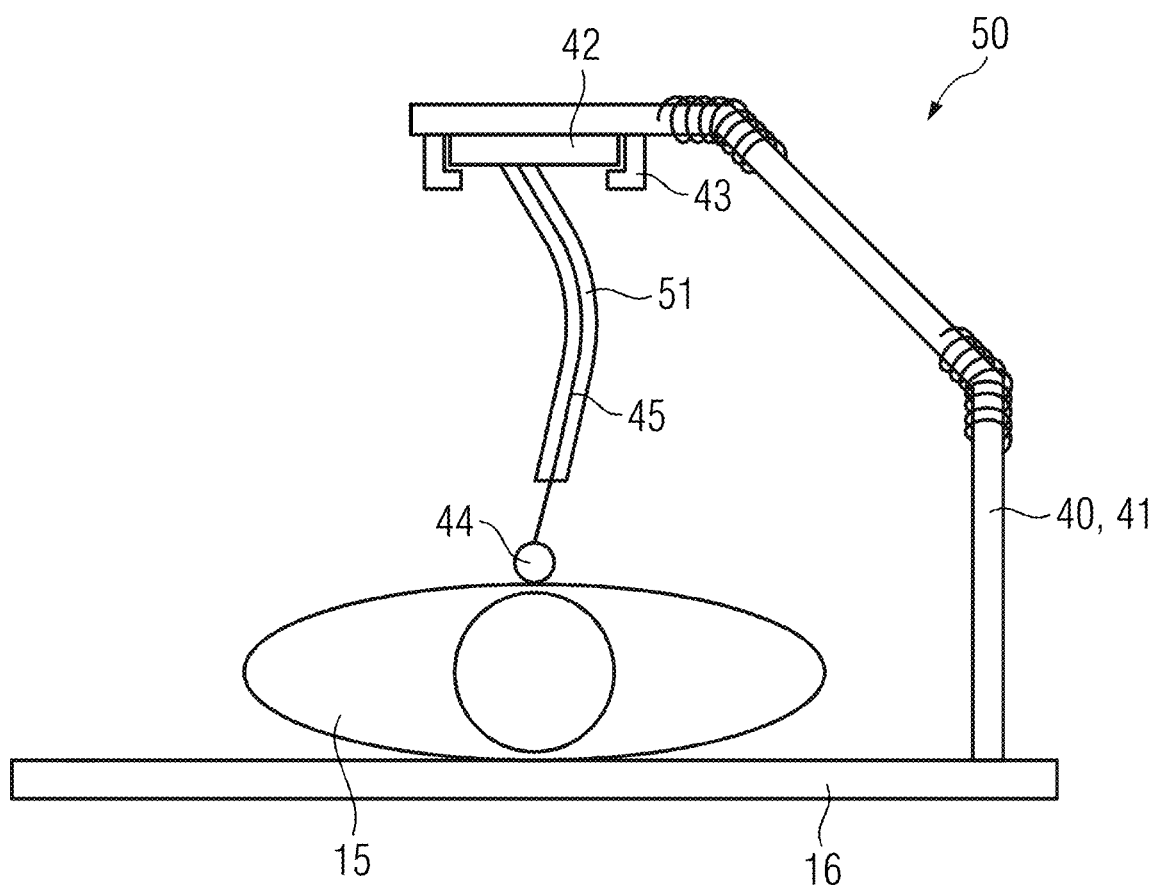
FIG. 3 shows a third aspect of an ECG device according to the disclosure in a schematic representation.

FIG. 3 shows a third aspect of an ECG device 50 according to the disclosure in a schematic representation. The third aspect differs from the first and second aspect in the carrier unit 40 which comprises a manually stiffly shapeable carrier structure 41.

Figure 4:
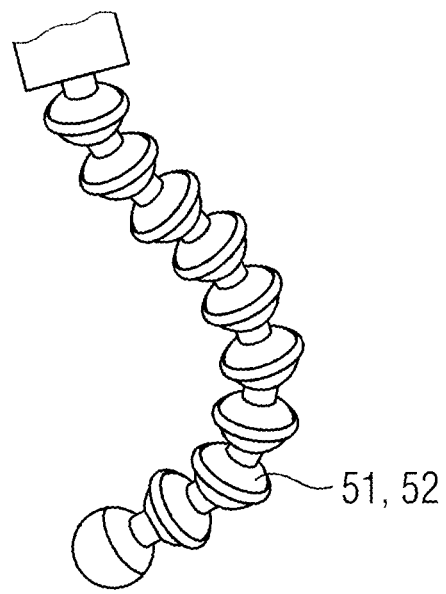
FIG. 4 shows an aspect of a shapeable guide element in a schematic representation.

FIG. 4 shows an aspect of a shapeable guide element 51 in a schematic representation in which the shapeable guide element 51 is designed for a stabilizing effect as flexibly mutually engaging and connected hemispheres and/or spheres 52. The shapeable guide element 51 can alternatively and/or additionally comprise one of the following components: MR-insensitive metal wire; aluminum wire; and copper wire.

Figure 5:
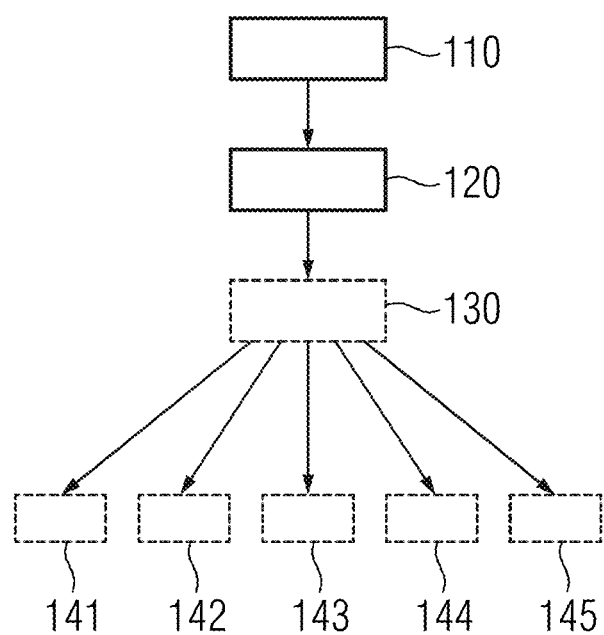
FIG. 5 shows a flow diagram of an aspect of a disclosed method.

FIG. 5 shows a flow diagram of an aspect of a disclosed method for capturing an ECG signal of an examination object 15 using an ECG device 50 according to the disclosure in combination with a capture of MR signals of the examination object 15 by means of a magnetic resonance device 11 according to the following method steps: method step 110 provides for capturing an MR signal of the examination object 15. In method step 120, the capturing of an ECG signal of the examination object 15 takes place. One aspect comprises method step 130, which provides for a capturing of a movement of the electrode conductor 45, wherein after a captured movement of the electrode conductor 45, at least one of the following method steps is carried out: method step 141, a rejection of the ECG signal; method step 142, a correction of the ECG signal; method step 143, an indication of the movement to the magnetic resonance device 11; method step 144, a rejection of the MR signal; and method step 145, a correction of the MR signal.

Figure 6:
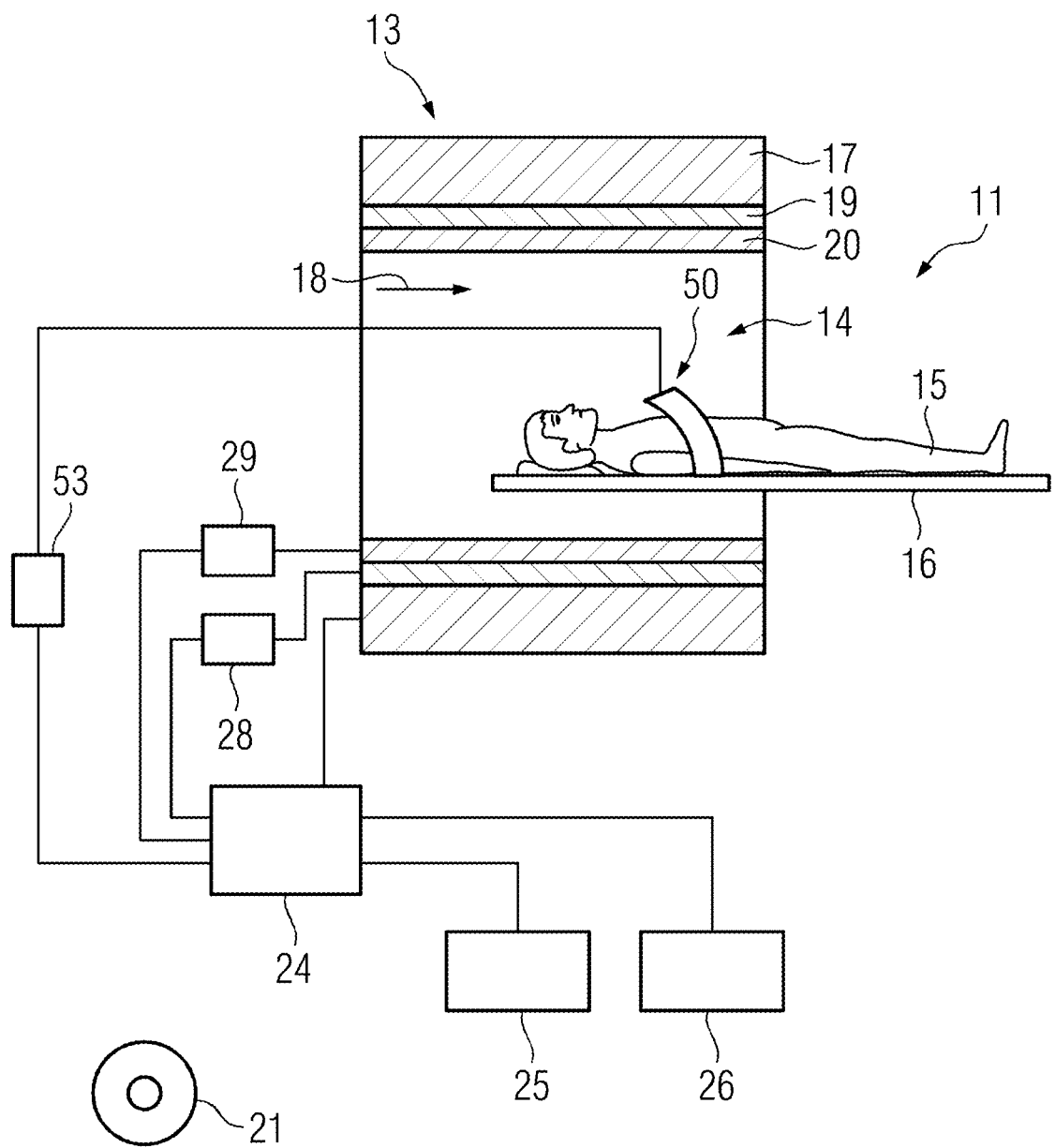
FIG. 6 shows a magnetic resonance device according to the disclosure in a schematic representation.

FIG. 6 shows a magnetic resonance device 11 according to the disclosure in a schematic representation. The magnetic resonance device 11 comprises a detector unit 13 designed to record an MR signal of an examination object 15 which is arranged within a patient receiving region 14 at least partially surrounded by the detector unit 13. In addition, the magnetic resonance device 11 further comprises an ECG device 50 according to the disclosure, said ECG device 50 being arranged within the patient receiving region 14 and being designed to capture an ECG signal from the examination object 15.

The detector unit 13 comprises a main magnet 17 for generating a static main magnetic field 18 of at least 0.5 tesla, preferably at least 1.4 tesla, particularly preferably at least 2.9 tesla. In addition, the magnetic resonance device 11 has a cylindrical patient receiving region 14 for receiving an examination object 15, wherein the patient receiving region 14 is cylindrically enclosed in a circumferential direction by the detector unit 13. The examination object 15 can be pushed into the patient receiving region 14 by means of a patient positioning apparatus of the magnetic resonance device 11. For this purpose, the patient positioning apparatus has a patient table 16 which is movably arranged within the magnetic resonance device 11.

The detector unit 13 also has a gradient coil unit 19 which can be used for a position encoding during an imaging process. The gradient coil unit 19 is actuated by means of a gradient control unit 28. Furthermore, the detector unit 13 has a radio frequency antenna unit 20 which, in the case shown, is configured as a body coil firmly integrated into the magnetic resonance device 11, and a radio frequency antenna control unit 29 for an excitation of a polarization which occurs in the main magnetic field 18 generated by the main magnet 17. The radio frequency antenna unit 20 is actuated by the radio frequency antenna control unit 29 and radiates radio frequency pulses into an examination space which is substantially formed by the patient receiving region 14.

The magnetic resonance device 11 additionally comprises an inventive ECG device 50 which is to be arranged within the patient receiving region 14, preferably touching the examination object 15. The magnetic resonance device 11 preferably comprises an ECG control unit 53 which is arranged outside the patient receiving region 14. The ECG control unit 53 is preferably designed to control an interaction between the ECG device 50 and the magnetic resonance device 11, in particular, dependent upon a captured movement of the electrode conductor 45. The ECG control unit 53 can also be designed for triggering an MR control sequence on the basis of an ECG signal captured by the ECG device 50. The ECG control unit 53 is typically connected to the ECG device 50. The ECG control unit 53 can be included by the ECG device 50.

The magnetic resonance device 11 has a control unit 24 for controlling the main magnet 17, the gradient control unit 28 and the radio frequency antenna control unit 29. The control unit 24 centrally controls the magnetic resonance device 11, for example, the execution of MR control sequences. The magnetic resonance device 11 has a display unit 25. Control information such as, for example, control parameters and reconstructed image data and/or ECG signals can be displayed for a user on the display unit 25, for example, on at least one monitor. In addition, the magnetic resonance device 11 has an input unit 26 by means of which information and/or control parameters can be input by a user during a scanning procedure. The control unit 24 can comprise the gradient control unit 28 and/or the radio frequency antenna control unit 29 and/or the display unit 25 and/or the input unit 26 and/or the ECG control unit 53. The control unit 24 is typically connected to the ECG control unit 53. The ECG control unit 53 can further comprise a movement correction unit (not shown).

The control unit 24 and the ECG control unit 53 are also designed to carry out a disclosed method for capturing an ECG signal and MR signals. For this purpose, the control unit 24 and/or the ECG control unit 53 have computer programs and/or software which are loadable directly into a memory store unit (not disclosed in detail) of the ECG control unit 53, with program means in order to carry out a disclosed method when the computer programs and/or software are carried out in the control unit 24 and/or the ECG control unit 53. For this purpose, the control unit 24 and/or the ECG control unit 53 have a processor (not disclosed in detail) which is configured to carry out the computer programs and/or software. Alternatively, the computer programs and/or software can also be stored on an electronically readable data carrier 21 configured separately from the control unit 24 and/or the ECG control unit 53, wherein a data access by the control unit 24 and/or the ECG control unit 53 to the electronically readable data carrier 21 can take place via a data network.

The magnetic resonance device 11 disclosed can naturally comprise further components that magnetic resonance devices 11 typically have. A general functional method of a magnetic resonance device 11 is also known to a person skilled in the art, so that a detailed description of the further components is omitted. Thus, the magnetic resonance device 11 is configured, together with the ECG control unit 53 and the control unit 24, for carrying out a disclosed method.

A disclosed method can also exist in the form of a computer program product which implements the method on the ECG control unit 53 and/or the control unit 24 when it is executed on the ECG control unit 53 and/or on the control unit 24. An electronically readable data carrier 21 with electronically readable control information items stored thereon can also be provided, said control information items comprising at least a computer program product such as just described and being configured, on use of the data carrier 21 in a control device 24 and/or an ECG control unit 53 of a magnetic resonance device 11, to carry out the method described.

Although the disclosed aspects has been illustrated and described in detail based upon the preferred exemplary aspects, the disclosed aspects are not restricted by the examples given and other variations can be derived therefrom by a person skilled in the art without departing from the protective scope of the disclosure.

The invention claimed is:

1. An electrocardiography (ECG) device designed for use in combination with a magnetic resonance device, comprising:
 a carrier unit designed to mount on a patient table;
 a receiving unit designed to mount on the carrier unit such that during an examination the receiving unit is above an examination object at a defined spacing from the patient table;
 an electrode; and
 an electrode conductor connecting the electrode to the receiving unit,
 wherein the electrode conductor is stabilized at least partially by way of a shapeable guide element.

2. The electrocardiography (ECG) device as claimed in claim 1, wherein the shapeable guide element comprises a stabilizing component selected from a group of components consisting of:
 MR-insensitive metal wire; aluminum wire; and copper wire and flexibly mutually engaging and connected hemispheres and/or spheres.

3. The electrocardiography (ECG) device as claimed in claim 1, wherein the shapeable guide element has a length of between 5 cm and 25 cm.

4. The electrocardiography (ECG) device as claimed in claim 1, wherein a length of the shapeable guide element corresponds to at least 80% of the length of the electrode conductor.

5. The electrocardiography (ECG) device as claimed in claim 1, wherein starting from an end of the electrode conductor adjoining the electrode, between 0.3 cm and 3 cm of the electrode conductor is free of a stabilization by the shapeable guide element.

6. The electrocardiography (ECG) device as claimed in claim 1, wherein the carrier unit comprises a fixing unit designed to accommodate the receiving unit.

7. The electrocardiography (ECG) device as claimed in claim 1, wherein the carrier unit comprises a manually stiffly shapeable carrier structure.

8. The electrocardiography (ECG) device as claimed in claim 1, wherein the carrier unit comprises a stable frame to position above a ribcage of the examination object.

9. The electrocardiography (ECG) device as claimed in claim 1, comprising:
 a movement sensor unit arranged on the electrode conductor and/or the shapeable guide element, designed to capture a movement of the electrode conductor.

10. The electrocardiography (ECG) device as claimed in claim 9, wherein the movement sensor unit comprises a movement detection unit and a first electrical conductor, and the movement detection unit is designed to capture the movement of the electrode conductor based on a continuous measurement of an electrical resistance in the first electrical conductor.

11. A magnetic resonance (MR) device, comprising:
 a detector unit designed to record an MR signal of the examination object which is arranged within a patient receiving region which is at least partially surrounded by the detector unit; and
 an electrocardiography (ECG) device as claimed in claim 1, the ECG device being arranged within the patient receiving region and being designed to capture an ECG signal from the examination object.

* * * * *